(12) United States Patent  
Walpole et al.

(10) Patent No.: US 12,057,201 B2
(45) Date of Patent: Aug. 6, 2024

(54) INTELLIGENT PLANNING, EXECUTION, AND REPORTING OF CLINICAL TRIALS

(71) Applicant: ZS Associates, Inc., Evanston, IL (US)

(72) Inventors: Kim Marie Walpole, San Diego, CA (US); Michael Joseph Nicoletti, San Diego, CA (US); Joshua Michael Stanley, San Diego, CA (US); Jason Edward Wallace, San Diego, CA (US); Thomas Ian Walpole, San Diego, CA (US); David Bruce Fogel, La Jolla, CA (US)

(73) Assignee: ZS Associates, Inc., Evanston, IL (US)

( * ) Notice: Subject to any disclaimer, the term of this patent is extended or adjusted under 35 U.S.C. 154(b) by 0 days.

(21) Appl. No.: 18/137,395

(22) Filed: Apr. 20, 2023

(65) Prior Publication Data

US 2023/0260604 A1    Aug. 17, 2023

Related U.S. Application Data

(63) Continuation of application No. 17/718,053, filed on Apr. 11, 2022, now abandoned, which is a
(Continued)

(51) Int. Cl.
*G16H 10/20*     (2018.01)
*G06N 3/08*      (2023.01)
(Continued)

(52) U.S. Cl.
CPC ............... *G16H 10/20* (2018.01); *G06N 3/08* (2013.01); *G06N 20/00* (2019.01); *G16H 10/60* (2018.01);
(Continued)

(58) Field of Classification Search
CPC ........ G16H 10/20; G16H 10/60; G16H 15/00; G16H 40/20; G16H 50/20; G16H 50/30;
(Continued)

(56) References Cited

U.S. PATENT DOCUMENTS 11,328,795 B2    5/2022  Walpole et al.
2016/0203296 A1*  7/2016  Bound ................... G16H 10/20
                                                          705/3
(Continued)

FOREIGN PATENT DOCUMENTS

WO    WO-2008/060287 A1    5/2008
WO    WO-2008060287 A1 *   5/2008    ........... G06F 19/345

OTHER PUBLICATIONS

Medidata (May 2018), White Paper "Using Patient Burden Evaluation to Improve Clinical trial Planning and Execution," https://www.medidata.com/wp-content/uploads/2018/10/Using-Patient-Burden_White-Paper_201805_Medidata.pdf, 7 pages (Year: 2018).*

*Primary Examiner* — Joy Chng
(74) *Attorney, Agent, or Firm* — Foley & Lardner LLP

(57) ABSTRACT

Machine learning based methods for planning, execution, and reporting of clinical trials, incorporating a patient burden index are disclosed. In one aspect, there is a method for determining a patient burden index. The method includes parsing a protocol for a clinical trial. The method further includes providing factor data for each of a plurality of patients. The method further includes calculating a patient burden index for each of the plurality of patients based on the parsed protocol and the provided factor data for each of the plurality of patients.

20 Claims, 11 Drawing Sheets

Related U.S. Application Data continuation of application No. 16/239,451, filed on Jan. 3, 2019, now Pat. No. 11,328,795.

(60) Provisional application No. 62/613,713, filed on Jan. 4, 2018.

(51) Int. Cl.
| | |
|---|---|
| *G06N 20/00* | (2019.01) |
| *G16H 10/60* | (2018.01) |
| *G16H 15/00* | (2018.01) |
| *G16H 40/20* | (2018.01) |
| *G16H 50/20* | (2018.01) |
| *G16H 50/30* | (2018.01) |

(52) U.S. Cl.
CPC .............. *G16H 15/00* (2018.01); *G16H 40/20* (2018.01); *G16H 50/20* (2018.01); *G16H 50/30* (2018.01)

(58) Field of Classification Search
CPC ........... G06N 3/08; G06N 20/00; G06N 3/04; G06N 3/126; G06N 5/048; G06N 7/02
USPC ........................................................ 705/2–3
See application file for complete search history.

(56) References Cited

U.S. PATENT DOCUMENTS

2017/0132396 A1* 5/2017 Bechtold ................ G16H 50/20
2017/0154166 A1* 6/2017 Klein .................. G06F 21/6245

* cited by examiner

INTELLIGENT PLANNING, EXECUTION, AND REPORTING OF CLINICAL TRIALS

CROSS REFERENCE TO RELATED APPLICATIONS

The present application claims the benefit of priority as a continuation to U.S. patent application Ser. No. 17/718,053, filed Apr. 11, 2022, which claims the benefit of priority as a continuation to U.S. patent application Ser. No. 16/239,451, filed Jan. 3, 2019, which claims the benefit of priority to U.S. Provisional Patent Application No. 62/613,713, filed Jan. 4, 2018, the entirety of each of which is incorporated by reference herein.

TECHNICAL FIELD

The present disclosure generally relates to machine learning for planning, execution, and reporting of clinical trials, incorporating a patient burden index.

BACKGROUND

The clinical trials process is costly, time-intensive, and replete with failures. In the USA, only 32% of drugs survive Phase I and Phase II trials, proceeding then to Phase III, and only 10% of potential drugs get approval. The cost of these failures is not known precisely but is estimated between $800 million and $2.4 billion per trial. Phase III failures are due primarily to poor efficacy, unanticipated adverse events or serious adverse events, or a failure to demonstrate commercial viability. Drugs also fail to be approved because of insufficient information provided to regulatory agencies, estimated at about 50% of new molecular entities applications.

Poorly constructed protocols lead to poor research, and potentially numerous costly amendments, protocol deviations, delays in obtained appropriate data, and other problems. Protocol deviations are not rare, estimated between 15.6% and 24.9% of all enrolled patients in studied Phase III trials. Furthermore, failure to report protocol deviations is a present issue: In a recent study, 32% of included trials did not provide any explicit reports of any type of protocol deviation.

Clinical trials involve a complex process of protocol design, scheduling, implementation, analysis, and reporting. In most cases this complexity is addressed by human experts, but this requires tremendous time and expertise. This expertise is also typically directed to one portion of the complex process, and may cause unintended issues in other portions. Moreover, it may be difficult to recruit and retain trial participants through the course of a trial. For example, one in four cancer trials fail to enroll and retain sufficient patients.

SUMMARY

Systems, methods, and article of manufacture, including computer program products, are provided for calculating a patient burden index for a clinical trial. In one aspect, a method includes parsing a protocol for a clinical trial. The method further includes providing factor data for multiple patients. The method further includes calculating a patient burden for each patient based on the parsed protocol and the provided factor data for each patient.

In optional variations one or more additional features, including but not limited to the following, can be included in any feasible combination. For example, parsing the protocol for the clinical trial may include analyzing a protocol document using keyword analysis and pattern matching. Parsing the protocol for the clinical trial may include generating a schedule of actions to be taken in the clinical trial. The factor data may include patient data, trial cost data, trial time data, trial content data, trial schedule data, and/or trial conduct data. The patient data may include age, gender, insurance status, marital status, number of children, and/or insurance coverage. The trial cost data may include transportation cost, lost work cost, and/or unreimbursed medical costs. The trial time data may include travel time, waiting time, and/or direct trial participation time. The trial content data may include observation by trial clinician, monitoring of vital signs, and/or blood draws. The trial schedule data may include trial events at scheduled dates and times. The trial conduct data may include empathy of trial personnel, understandability of trial materials, rigidity of scheduling, physical discomfort associated with trial events, and/or fatigue associated with trial events. The patient burden index may correspond to an absolute level of burden on the patient participating in the trial, a probability of retention of the patient in the trial to completion, a probability that the patient will offer positive comments about the trial, and/or a probability that the patient will offer positive comments about a principal investigator or a staff member of the trial. The method may further include training a machine learning system with a training observations of historic patient factor data and historic patient burden data. The machine learning system may include a neural network, a rule based system, a linear regression system, a non-linear regression system, a fuzzy logic system, a decision tree, a nearest neighbor classifier, and/or a statistical pattern recognition classifier. The neural network may further include input nodes, hidden nodes, and at least one output node. Input nodes may be connected to hidden nodes. Hidden nodes may be connected to the at least one output node. The method may include inputting the factor data for the plurality of patients into the trained neural network and outputting, from the at least one output node, the patient burden index for each of the plurality of patients. The method may further include generating a rule base that associates the patient factors with the patient burden index. The rule base may include fuzzy rules. The method may further include modifying the protocol to reduce the patient burden index.

Systems and methods consistent with this approach are described as well as articles that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
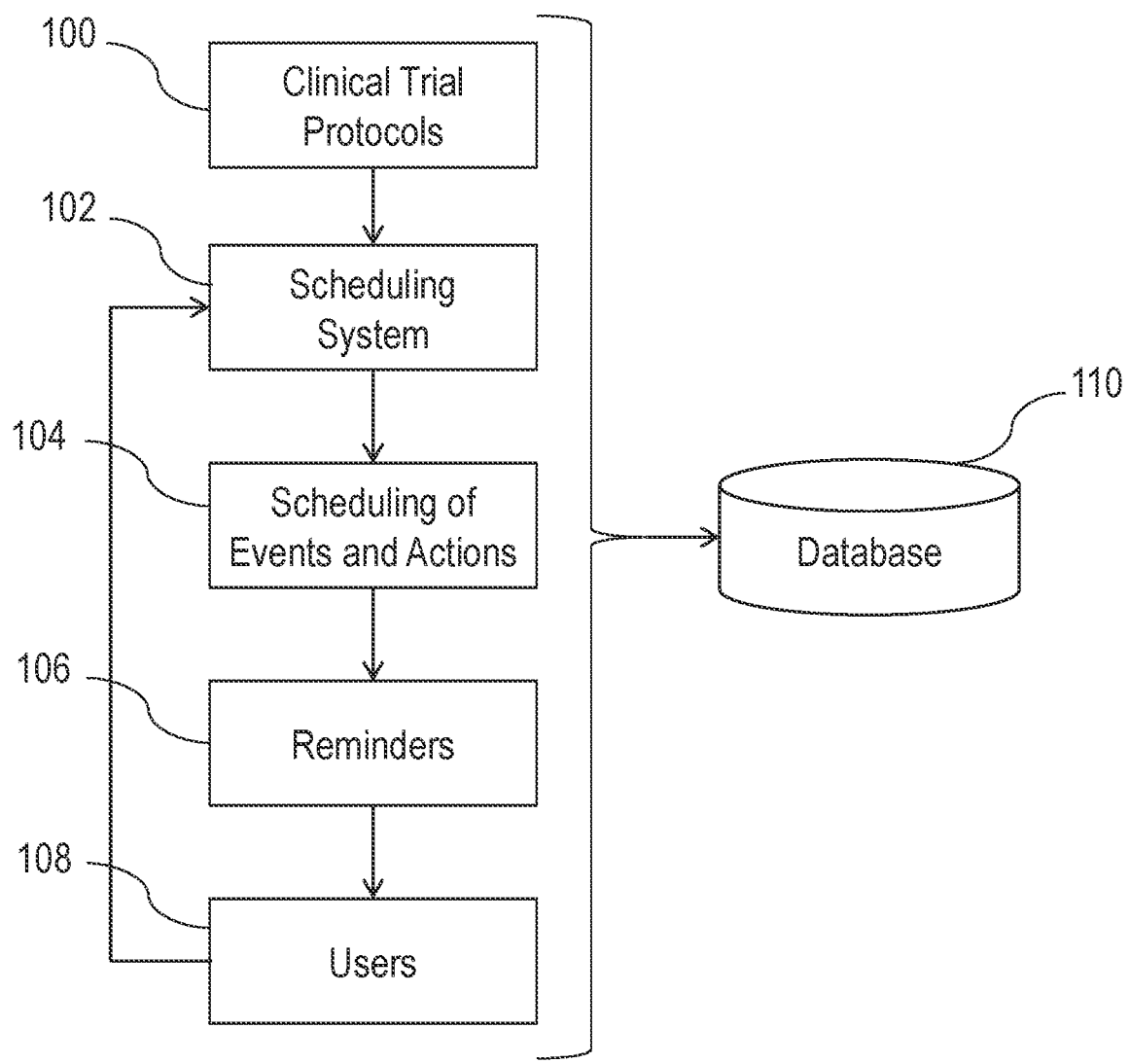
FIG. 1 illustrates an example of a clinical trial protocol information chain.

Advances in artificial intelligence, machine learning, and other data analytic techniques make it possible to improve the intelligent planning, execution, and reporting of clinical trials. Artificial intelligence, machine learning, and other data analytic techniques make it possible to improve the design and execution of research protocols for clinical trials, and improve trial participant recruitment and retention.

For example, AI methods can be created to accept a protocol document, scan it, and assess it for various characteristics of interest. This includes, for example, consistency between a calendar-based schedule, for example expressed as a time and events (T&E) table, and the in-text description of events, and consistency between the synopsis and the body of the protocol. Natural language processing tools can also be helpful in this regard. The disclosed technology employs AI techniques to address each of these opportunities.

In addition, the disclosed technology employs AI to scan other published protocols based on a similarity measure, which may include criteria such as the indication for treatment, primary and secondary objectives, whether or not the study involves pharmacokinetics and pharmacodynamics, safety objectives, whether the study involves a drug or a device, the type of study (e.g., randomized, blinded), and so forth. Similar protocols can then be coupled with published or internal data indicating the degree of success from the experimental design as well as any problematic items. Concerns can then be flagged for the study designer for further consideration.

Moreover, the disclosed technology utilizes AI methods to warn the study designer of potentially problematic issues, for example, that particular inclusion/exclusion criteria may be too limiting for subject enrollment. In addition, the disclosed technology incorporates a measure described as a participant or patient burden index (PBT), which is an AI-derived quantitative measure of the impact that the protocol design has on the patient or subject.

The burden that patients undergo has a significant correlation to retention, that is, having patients stay in a clinical trial all the way to completion. For the purposes of this description, the term patient is understood to include persons who have a particular medical condition, normal healthy subjects or others who would be termed subjects, consumers in the public in the case of an over-the-counter medication, or anyone else who may participate in a research study.

The disclosed technology also benefits from mapping the T&E schedule into a dashboard-driven user interface that shows when each event is to be completed. With available personnel assignments and schedules, the system can also identify who is to do which task in support of which patient at which time. Practitioners are alerted ahead of time for windows for events, which may help reduce protocol deviations. The disclosed technology also notes deviations from the protocol and requires the investigator or other approved personnel to offer a written explanation.

To facilitate participation, the disclosed technology is designed to alert study participants, by email, phone, or text, to remind them of study events. This may assist in maintaining study compliance, creating fewer protocol deviations, and generating greater subject retention. The system then provides an estimate of the likelihood to complete the study, which may help the study coordinator maintain cognizance over the trial.

Medical errors and inappropriate medical attention remain an issue in medical practice. The disclosed technology helps reduces these problems by storing the patient's medical history and concomitant medications and searches for possible allergic reactions, drug interactions, or other issues. It also assesses appropriate dosing or mis-dosing, as well as analyzes any possible inappropriate medications to treat a treatment-emergent adverse event, even if it may the standard of care for the study site.

Principal investigators must assess adverse events for potential relation to a study drug. The disclosed technology assists the investigator by analyzing adverse events and assessing the plausibility or possibility of a relation. The result can be conveyed via fuzzy logic and a linguistic description. Suggested treatments for adverse events can be suggested in the disclosed technology based on analysis of standard of care and individual subject needs, which could include insights from genomic data. In addition, the disclosed technology provides the investigator with the opportunity to easily review all serious adverse events or other adverse events of special interest, and assists in creating a condensed narrative in better anticipation of what may be appropriate in a clinical study report.

In the disclosed technology, data are collected and the system may aggregate the data according to the statistical analysis plan associated with the protocol, again in anticipation of what may be appropriate in a clinical study report.

FIG. 1 illustrates an example of a clinical trial protocol information chain. Clinical trial protocols 100 are provided to a scheduling system 102 that is capable of parsing the protocols into actions relative to a calendar. This includes site-specific information about the trials, which subjects are to be included, who the principal investigator of the trial will be, and other pertinent information. The actions to be taken in the trial, as described by the protocol, are used to generate a calendar-based schedule expressed as a time and events (T&E) table 104 for the clinical trial. Alternatively, the T&E table may be provided outside of the system.

One method for parsing a protocol is based on keyword analysis, in which pattern matching is used to locate predefined standardized pertinent sections of a protocol. Each of these sections contains specific information, known to be associated with a particular subtopic in the protocol, such as the principal investigator's name and contact information, or the time and events schedule for actions to be taken during the protocol. Subsections on eligibility define which subjects are to be included or excluded, typically designated by age range, gender, medical conditions, and ability to provide informed consent.

A calendar or timeline of a trial can be extracted from the time and events as found in two locations in a standard protocol. These data are presented in tabular form and in text. Action items can be constructed algorithmically for each indication in the time and events table, checked against the language in the text for consistency. Different procedures have typical associated events. For example, pharmacokinetic/pharmacodynamics (PK/PD) studies have specified time points at which blood must be drawn. This would not generally be anticipated in a study on post-surgical pain, in contrast. By using predefined classes of investigations, algorithms can more easily and reliably extract the pertinent information in a T&E table and text, and construct the framework that will guide the practitioner through the conduct of the trial.

As a trial is conducted, and in light of the T&E table, the scheduling system issues reminders 106 to users 108 of the system. The reminders can have the form of electronic messages to remind a study coordinator to arrange for a specific doctor to be on call, or to remind a subject to adhere to their course of medicine, or to remind personnel involved with supply chain management to deliver required medications on time to clinical trial facilities, or any other pertinent actions associated with the conduct of the trial. The users of the system can be at many levels associated with a clinical trial: subjects, practitioners, healthcare providers, principal investigators, study coordinators, sponsors, or other entities. Each actual user is associated with the scheduling system. Data associated with each associated person may be maintained in the system, including for example the curriculum vita of the investigators, consent forms, medical history forms, and so forth. The entire information chain from protocols 100 to reminders 106 to users 108 is stored in a database 110 which may include online and offline characteristics, which may be synced at appropriate times, for further use as will be explained below. In the case of a protocol amendment, the approved amendment is used to update the T&E table and all new events are sent to all investigators, with details on the difference between the prior and new protocol, described in a summary of changes. Tasking is updated and investigators may need to confirm receipt of the amendment.

To facilitate system use, a graphical user interface provides data using graphic displays, including timelines, circles for events during a day, colors for warning and other associated meanings, and icons that describe a given activity. For example, if a blood draw is due on a particular subject within the next 30 minutes, this event may be displayed in green. It may change to yellow if the blood draw is overdue by up to maximum allowable window of time as designated in the protocol. After that it may change to red, signifying the event is past due and constitutes a protocol deviation. The graphical user interface also provides the means for comparing sites or study groups using bar charts, pie charts, or other charts. Such comparisons could include retention rates, protocol deviation rates, as well as costs.

Figure 2:
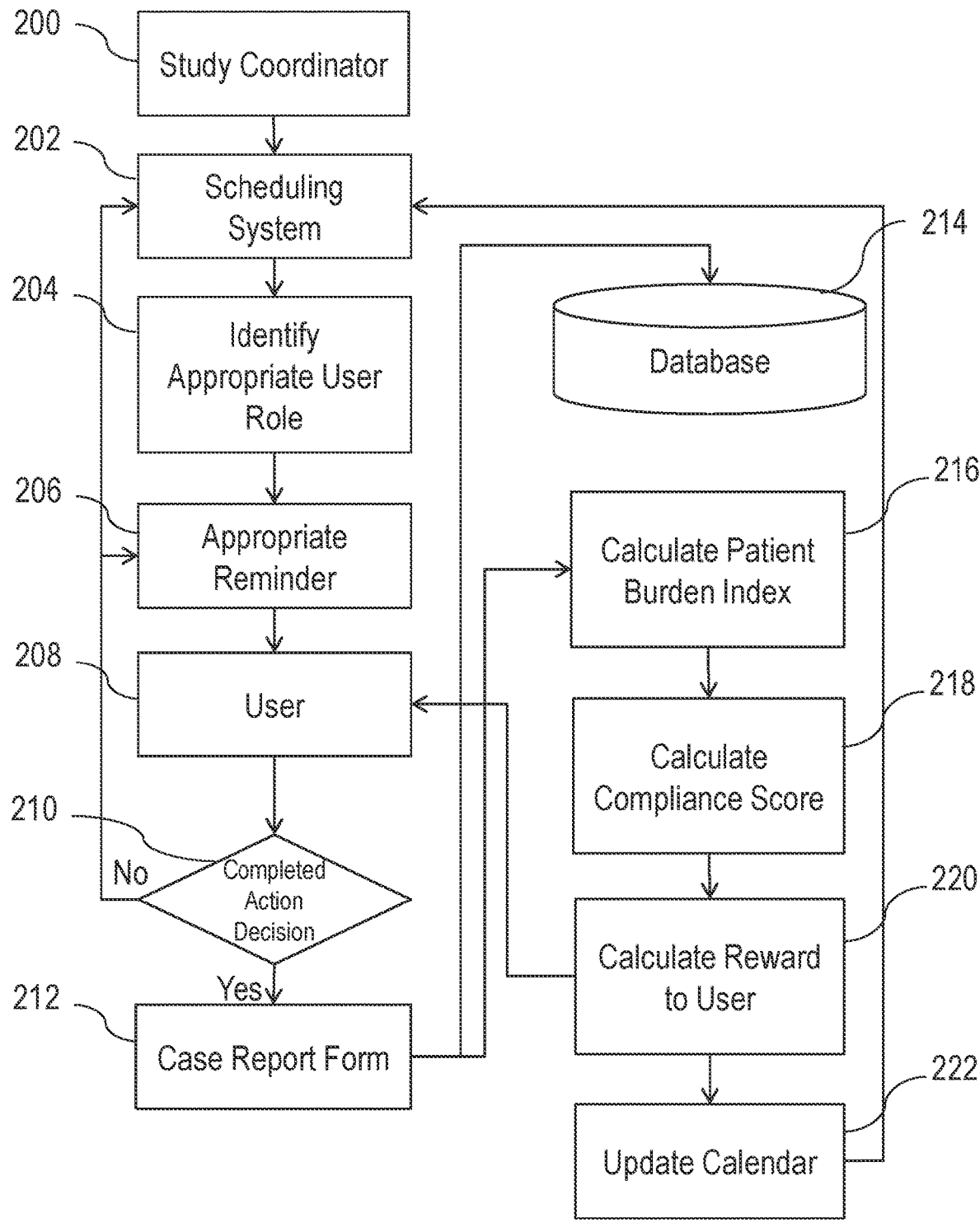
FIG. 2 illustrates an example of a coordinator system.

FIG. 2 illustrates an example of a coordinator system. From the point of view of the study coordinator 200, when the coordinator accesses the scheduling system 202, the coordinator may identify appropriate user roles 204 for all users in the system. In accordance with the previously described T&E table, the system sends an appropriate reminder 206 to a user 208. All communication between the study coordinator and the subjects can be handled through the system, which may include email, text, phone/voice mail, and also notifying associated persons. The system may also handle the distribution of remuneration as appropriate for subjects. Should the user complete the required action in the appropriate amount of time 210, a case report form 212 is updated and completed and added to a database 214 of information. Should the user not complete the required action in the appropriate time, additional reminders are sent, and the scheduling system is adjusted to reflect improper user behavior. Notification is sent to the study coordinator identifying the delay caused by the user or associated with the event.

Prior to the beginning of the trial, and after each reminder and action, and following the actions of each users, the system calculates a patient burden index 216 which represents the overall burden for each patient in the clinical trial. The patient burden index 216 may be the result of a mathematical function that includes the results of machine learning applied to data associating subject-related factors and self-reported or imputed levels of burden, and may also combine domain expertise in the form of explicit knowledge or rules.

The system also may calculate a compliance score 218 which is a metric of how well each user is adhering to the required actions for the trial. Those users who have a sufficiently high compliance score may be provided with a reward 220 and the T&E calendar is updated 222 to reflect completed actions. The compliance score may assign points for each of the tasks that the user must perform. These points may be equal or unequal across all tasks, depending on the significance of the task. All of the information regarding user actions and score calculations is collected into a central database.

Patient burden encompasses different known factors that may be used to calculate a patient burden index 216. One such factor is financial burden. The financial impact to patients in clinical trials can be easily overlooked in clinical trial design, as attention is focused on the objectives, endpoints, and other aspects. But patients may have out-of-pocket costs when participating in a clinical trial. These include the cost of transportation and lost work, but also medical costs for additional testing. Insurance may not cover medical care beyond that which is deemed routine. Even when it does, deductibles are often quite high and a given patient may not be able to afford to participate.

Another burden includes the patient's investment of time. Often, patients in clinical trials must travel to and from study sites. This is a longstanding problem for elderly patients, but regardless of patient age, long travel times, particularly in urban areas, can dissuade participation. Research from the Washington State Office of Financial Management shows that most adults are willing to travel less than 30 minutes for other than routine care. But tolerance for time of travel differs by demographics: males versus females, insured vs. uninsured, being 65 or older vs. being under 65. The patient's time investment is also impacted by when visits are scheduled and are unique to the patient's individual circumstances. For example, there is significantly more burden on a single mother with school-aged children if a visit is scheduled for 3:30 pm (after school) than at 10:00 am (while her children are attending classes). Another instance of time burden involves wait times in study centers. Research shows that 30% of patients have left an appointment due to excessive wait times. Facilitating interactions with patients during their waits can reduce the perception of a long wait time.

Patient burden is also a function of the type of trial that is being undertaken, and specifically the events of the trial and the schedule of the events. Different treatments induce more or less discomfort, fatigue, or other factors that affect patient disposition. Alternative choices for clinical trial design can affect patient burden directly. For example, burden could be reduced in a trial by eliminating an extra blood draw, or reducing the number of required site visits.

Patient burden is also a function of the materials that are provided to the patient. Patient burden can be reduced by: (1) providing materials that are easy to understand, (2) having empathetic and supportive staff, (3) leadership and enthusiasm from the principal investigator, (4) a schedule (time and events) that works in synergy with the patient's constraints rather than at odds with those constraints, (5) the opportunity to adaptively reschedule visits and assign appropriate personnel to support participants, (6) trial management software to send effective reminders about visits and protocol adherence via phone, text, or email, including supporting multiple languages in multi-lingual areas, and (7) understanding what the patient's day-to-day experience during the trial is likely to be.

In various embodiments, calculating the patient burden index 216 is accomplished using machine learning methods based on the available data for some or all of financial costs, time investment, personal situation for time dependency, wait times, lack of personal interactions, physical discomfort or fatigue, lack of comprehension of provided materials, rigidity of scheduling, and/or other factors. These data are examples of independent factors (independent variables). Historical data regarding the association of these factors with actual retention in or withdrawal from clinical trials, or data regarding patient satisfaction, or other measures of realized patient burden, are examples of dependent factors (dependent variables).

In various embodiments, those factors thought to be associated with patient burden are delineated. Each factor is assigned point values that are presumed to be associated with a perceived increase or decrease in patient burden. For example, patient waiting time is known to be associated with patient burden. One possible point assignment is 0 points for wait times less than 20 minutes, 1 point for wait times between 20 and 25 minutes, and 2 points for wait times greater than 25 minutes. Across all assumed factors, points are assigned, and then summed to determine an overall point score. Patients are asked to assessed their own perceived level of burden, such as on a 10-scale, where 10 is the most burdened. Mathematical optimization algorithms, such as an evolutionary algorithm, can then be used to optimize the point assignments so as to best match the actual reported perceived level of burden.

For example, subject-related factors may be input into a multilayer neural network that responds with a projected likelihood of withdrawal during the trial. Research shows that various factors are associated with patient burden, including but not limited to: 1) waiting time prior to being seen, 2) driving time to and from the study center, 3) pain experienced during the try, 4) out-of-pocket cost to participate in the trial, 5) social engagement of the principal investigator and the study staff with the patient. Data regarding these and other factors can serve as inputs to a neural network, which is trained to respond with the presumptive overall patient burden.

Alternatively, a rule-base may be learned using methods such as C4.5 or evolutionary algorithms that associates input features with a numeric rating describing the patient burden, and the rule-base may include fuzzy and/or crisp rules. For example, a crisp rule may be in the form of "IF (patient is waiting more than 30 minutes) THEN (increase patient burden by 1 point)" A fuzzy rule may be in the form of "IF (patient is waiting a long time) THEN (increase the patient burden by a small amount)." In the case of fuzzy rules, an underlying mathematical logic translates a linguistic description such as "long time" into possible specific instances, such as specific durations in minutes. The fuzzy approach allows for more direct linguistic description more common to human communication.

In the case of a neural network approach, the specific architecture and neuronal transfer functions may be attained by a process of trial and error, or as a result of stochastic optimization using an evolutionary algorithm, or other method. For example, an evolutionary algorithm may start with a collection of alternative weights, transfer functions, and architectures for a neural network. Based on the effectiveness of assessing available inputs to generate desired outputs, a subset of the weights, transfer functions, and architectures that provide the greatest overall success are retained and then varied to create new weights, transfer functions, and architectures that are related to those that were most successful. These new designs are then tested and the process is iterated, eventually converging on a design that is deemed optimal for the expended computational effort.

A neural network may be optimized with respect to an objective function that describes the worth of predicting outcomes accurately or with some degree of error, forecasting either too high or too low, with potentially uneven penalties for these two types of error. For example, in the case of employing a neural network for measuring patient burden, the costs of predicting too high versus too low are unlikely to be symmetric. Predicting too high means that the actual burden the patient is undergoing is lower than estimated. This may result in more actions and cost to reduce a patient's burden than would be necessary. Predicting too low means that the actual burden the patient is undergoing is higher than estimated. This may result in the patient feeling uncared for, that the trial is too onerous, and may lead to the patient dropping out. It is important to use appropriate judgment when creating the objective function to that costs of these different types of errors are incorporated in the function. Data and model sufficiency may be assessed in part based on the performance of the designed neural network on test data held out from the training data.

Figure 3:
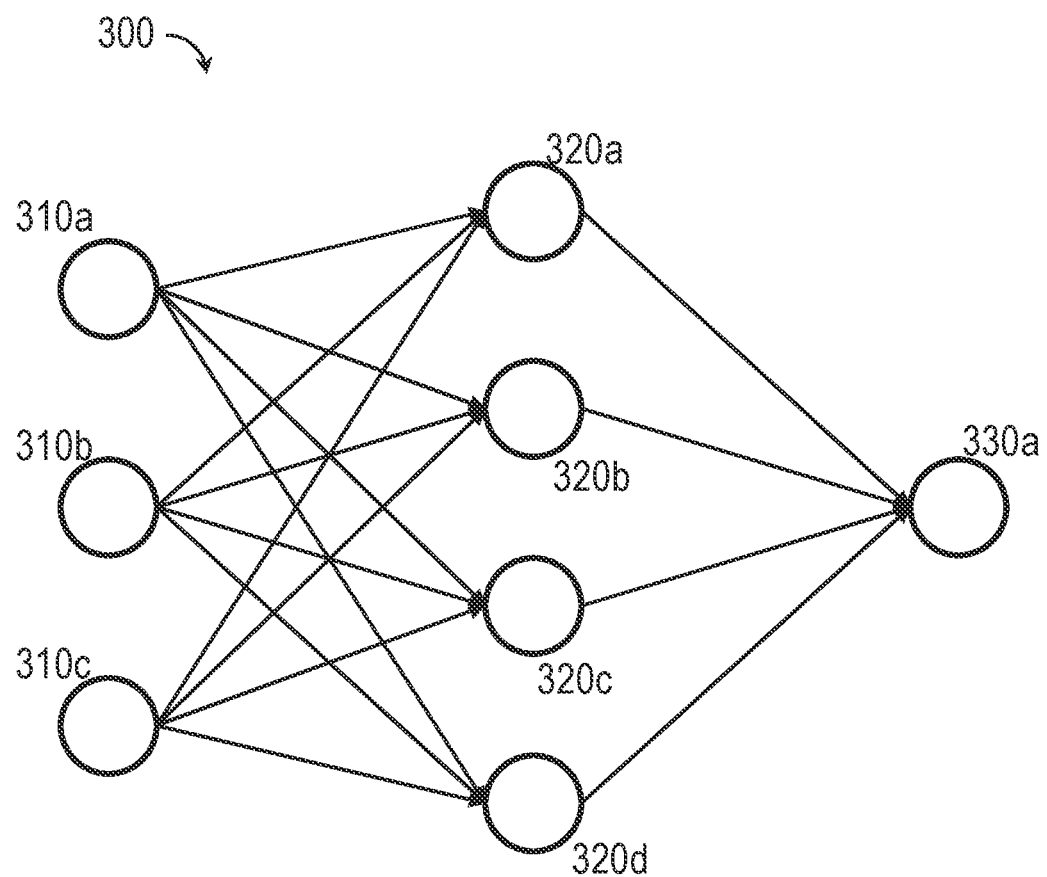
FIG. 3 illustrates an example of a neural network used to predict a level of patient burden given a set of independent factors.

Machine learning creates a useful mapping from the independent factors to the dependent factors, such that the mapping can be reused in future situations to predict the level of patient burden given a set of independent factors. As noted above, one such approach is to use neural networks or other hierarchical mathematical filters, which perform successive operations starting with the independent data and seek to match given dependent data. For example, one approach would be to create a neural network of the form in FIG. 3, where there are 3 input nodes 310a, 310b, and 310c, which could represent financial cost, maximum wait time, and ease of understandability of materials, and one output node 330a which describes the overall patient burden. The three inputs 310a, 310b, and 310c are connected to one layer of four hidden nodes 320a, 320b, 320c, and 320d that intervene between the inputs 310a, 310b, and 310c and the single output 330a. These hidden nodes 320a, 320b, 320c, and 320d employ mathematical transfer functions, such as having the form of a hyperbolic tangent. Other implementations may have a more or fewer input nodes, additional layers of hidden nodes, more or fewer hidden nodes, and/or more outputs. The successful design of neural network models requires not simply the algorithms for constructing the neural models, but appropriate preprocessing of the available data.

For the case of creating a patient burden index, the disclosed technology includes the following important advantages. One advantage is that input data can be described using various descriptors simultaneously. For example, the financial cost to a patient can be described by the actual cost, the cost relative to others in the same or similar circumstances, the cost relative to the patient's ability to pay, and perhaps other descriptions. Moreover, these descriptions can be provided in numeric descriptions, such as $5,000.00, or in linguistic description such as "very high" using fuzzy logic, which is then defuzzified using conventional methods to crisp numbers for the neural network to process.

Another advantage is that the machine learning method can search across these descriptors for those that are most apt to be useful for modeling.

Another advantage is that the output data, which represents patient burden, can be adjusted to represent an absolute level of burden, or a value that is associated with a particular outcome, such as the probability of retention to completion, the probability of offering positive comments about the study, the probability of offering positive comments about the principal investigator or the study staff, or any other dependent variable.

Another advantage is that machine learning can be used to evaluate an existing model, such as a neural network, to determine which independent variables are most important to improving a desired outcome. For example, suppose data are available for the patient's financial burden, maximum waiting time, and ease of interaction with study staff. Further suppose that the best mathematical model projects these data to be associated with a probability of staying in the clinical trial to completion of 0.75. The sponsor may seek to increase this probably by searching over the possible adjustments that could be made for the patient, such as easing the interaction with the study staff, ensuring minimal waiting times, or reducing the patient's cost. The search over these adjustments yields a response surface representing potential new probabilities of completing the trial. The sponsor can then use this as a decision tool to determine if it is worth investing time or funds to improve the situation for this patient, and thereby improve the likelihood of their being retained to completion.

The use of neural networks is not specific to this application. Other mathematical constructions could also be employed, including symbolic expressions, various forms of linear and nonlinear regression, fuzzy logic, and decision trees, not to exclude other possible mathematical forms. Similar applications of the invention can be employed on these other mathematical constructs.

In one approach, operationally, the process begins with determining the available data. A pharmaceutical company concerned about developing a measure of patient burden may have access to prior investigations that it has conducted in a similar area or in an earlier phase. Suppose this is the case for a drug that is under development in the area of pain management. Suppose further that the current trial being planned is a Phase 3 trial, following a successful Phase 2 trial. However, in the Phase 2 trial, the retention rate was 65%, meaning that 35% of patients did not complete the study. The pharmaceutical company wants to develop of model of patient burden in the Phase 2 trial so as to predict patient burden in the Phase 3 trial.

In the Phase 2 trial, suppose that 100 patients were enrolled, with 65 completing the study. To develop a measure of patient burden, the process starts with data from the Phase 2. All patient demographic data, including age, gender, ethnicity, height, weight, and BMI are available. Statistical hypothesis testing is used to determine if any of these factors are statistically significantly associated with a greater likelihood of withdrawing from the study than the baseline rate of 35%. Suppose that men are found to be more likely to withdraw in the Phase 2 study.

In addition, in the Phase 2 study, data are available on patient end-of-treatment satisfaction surveys. Suppose that patients who did not complete treatment during the trial were followed for adverse events throughout the defined duration of the study and provided answers to the survey. From these data it was found that the likelihood of withdrawing was inversely proportional to the number of interactions with study staff. Moreover, from the Phase 2 data, patients who were scheduled in the afternoon were twice as likely to withdraw from the study as were those who were scheduled in the morning.

The next step is to construct a mathematical model that relates the features associated with gender, number of study staff interactions, and scheduled appointment time, with the likelihood of patient withdrawal. Suppose it were desired to use a neural network for this purpose. The network is trained using a portion of the available data, mapping the inputs to an output of 1 or 0, representing whether or not the patient completed the study. This training could be accomplished by gradient methods, stochastic methods, or other methods. The process of training on a portion of the data and testing on a held-out portion of the data for validation is well described in common literature. However the training is accomplished, suppose that a network exists that offers the optimal mapping for the given data. Using the method of the disclosed technology, the model can now be probed to determine which changes in inputs would yield the greatest propensity to increase or decrease the network output, which is associated the likelihood of withdrawal. In the method of the disclosed technology, for a given patient presenting data such as {male, 5, 9:00 am}, assume attention is focused on the number of planned study staff interactions. For the available other data, the number of planned interactions can be adjusted up and down, with the output of the neural network observed. The process is halted when the value associated with the desired (in this case, maximum) output value is obtained. This then represents a potential optimization of the trial for the individual patient being considered.

In another embodiment of the invention, a model can be constructed to estimate the patient burden based on prior responses to satisfaction survey questions. Suppose that surveys in the prior Phase 2 study offered patients with the opportunity to state their satisfaction with the study, the study materials, and the tolerability of the drug being tested. These were rated on a traditional 7-point Likert scale (1=low, 7=high). Suppose attention is focused on the satisfaction with the study materials. The materials can be evaluated with respect to reading comprehension level, time required to complete reading the materials, and the sentiments associated with the materials. Reading comprehension level is determined by standard techniques, as is the time required to complete reading the materials. Measuring sentiment can be performed algorithmically using databases that associate words and phrases with different human emotions, such as anxiety, depression, or compassion.

Figure 4:
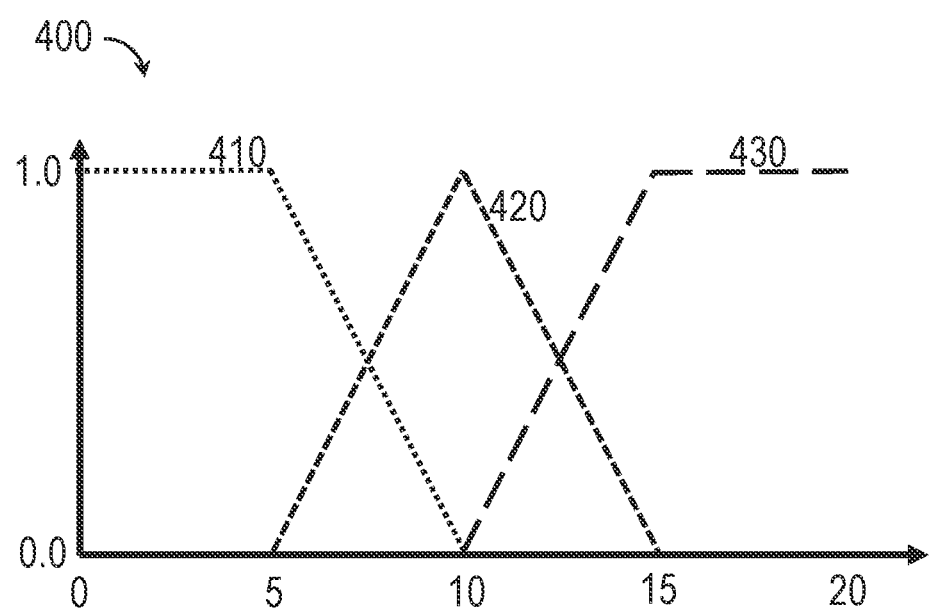
FIG. 4 illustrates an example of fuzzy sets associated with an emotion of anxiety that may be generated by a sentiment analysis system.

If the desire is to improve the overall response to subject satisfaction with study materials, in a manner similar to the prior example, a mathematical model can be constructed that maps the features describing the materials, along with, say, demographic information into the output associated with the patients' satisfaction ratings. However, rather than rely directly on numeric inputs, the inputs related to sentiment may be described linguistically, such as with descriptions of "low," "medium," or "high" with respect to associated emotions. This can be accomplished using fuzzy logic descriptions of the values associated with these emotions. FIG. 4 describes one possible set of fuzzy sets associated with an emotion of anxiety as might be generated by a sentiment analysis algorithm in graph 400. Here, the y-axis is the degree of membership in the set and the x-axis is the measured value of the emotion. FIG. 4 includes a low emotional membership function 410, a medium emotional membership function 420, and a high emotional membership function 430. The sum of the low, medium, and high membership functions 410, 420, and 430 equals one for each measured value of the emotion. Values below 5 are always associated with low emotion. Values between 5 and 10 are associated with either low or medium emotion. A value of 10 is associated with a medium emotion. Values between 10 and 15 are associated with medium or high emotion. Values above 15 are associated with high emotion. For example, a measured value of 7.5 corresponds to a membership 0.5 in the set of low emotional values as indicated by the low membership function 410, membership 0.5 in the set of medium emotional values as measured by the medium membership function 420, and membership 0.0 in the set of high emotional values as indicated by the high membership function 430. These descriptors can be used as input features for the mathematical model to map into the desired output, here associated with the satisfaction survey results.

Figure 5:
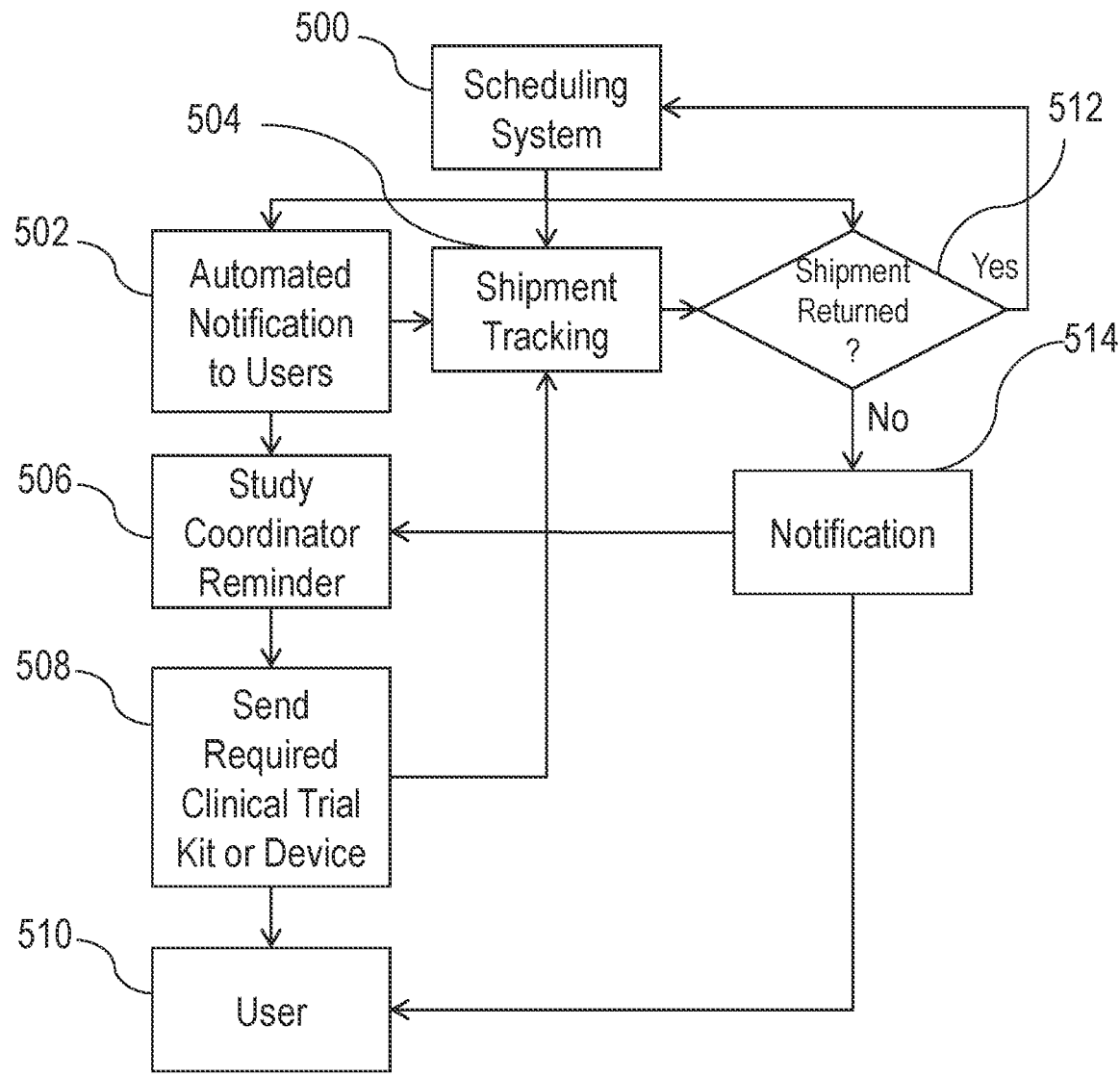
FIG. 5 illustrates an example of a supply chain system.

FIG. 5 illustrates an example of a supply chain system. Concurrently with the T&E calendar, the scheduling system 500 also supplies automated notifications to users 502 to send shipments of goods and materials to clinical study sites so that they arrive on time. These shipments are tracked 504 for delivery. The system reminds the study coordinator 506 to adjust any necessary components of the timing associated with sending a required clinical trial kit or device 508 to a user 510. If a shipment is not returned after use 512, a notification 514 is sent to the study coordinator and user as a reminder. Once a shipment is returned, the scheduling system is updated. All of the information regarding the scheduling system is fed to a central database.

Figure 6:
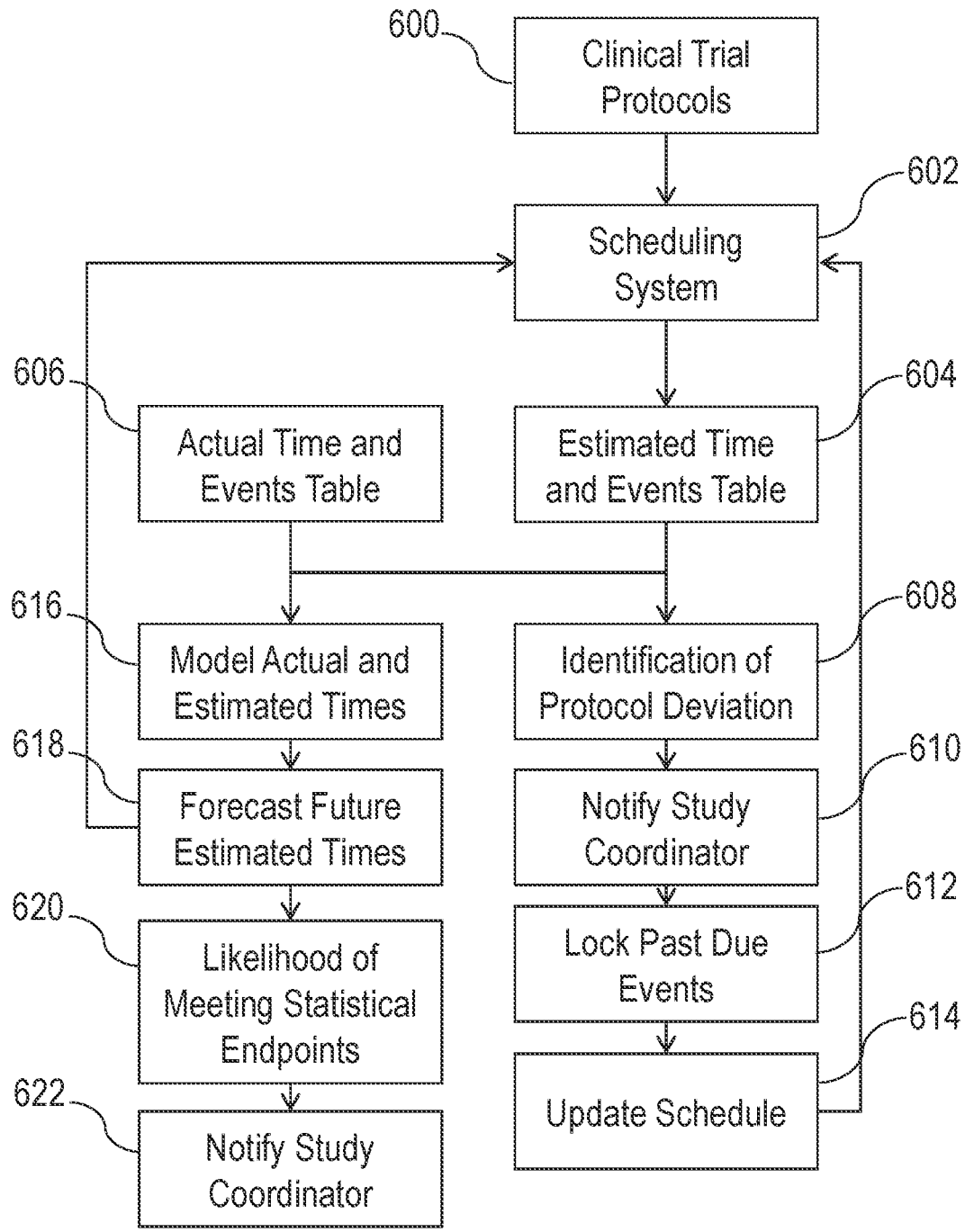
FIG. 6 illustrates an example of a scheduling system.

FIG. 6 illustrates an example of a scheduling system. When clinical trial protocols 600 are provided to the scheduling system 602, in light of the T&E table, and calendar, and rate of completed assignments, a new events table 604 can be generated for past, current, and future events. This can be compared to the actual T&E table 606 and a difference calculated. The difference is expressed as one measure of protocol deviation 608 which may help the study coordinator understand where processes are either ahead of schedule, operating on schedule, or behind schedule. A schedule may be created using an algorithm such as a so-called greedy algorithm, which schedules each next most beneficial next tasks in order, or by other methods such as evolutionary algorithms, in which alternative schedules are evaluated, competed, and improved in a process of variation and selection. The advantage of the former method is that it may be faster than the latter, whereas the latter may be more capable of finding more broadly appropriate schedules. The tempo of operations for the schedule can help determine which algorithmic approach to employ.

The study coordinator is notified 610 of any deviations and all other protocol deviations and allowed to lock past-due events 612 in the system so that they can be examined and recorded for their deviation as a part of responsible clinical trial management. Protocol deviations are automatically recorded for missing data, with responsible parties queried for an explanation. Parties who are responsible for past-due events may receive increasingly insistent messaging. The system may use rules or other artificial intelligence methods to determine the most likely effective means of communication with the responsible party. For example, algorithms may examine past patterns of prompts and determine which type is most likely to generate a desired action for the individual in question. The general plausibility of results may be checked by the system for reasonableness on an on-going basis with any deviations reported to the study coordinator and/or principal investigator.

The schedule of future actions to be taken under the trial is updated 614 and fed back to the scheduling system as such changes may have wide ranging effect. At the same time any deviation between the actual and estimated time and events table can be used to more accurately estimate both actual and estimated times 616 and generate a forecast for future estimated times 618 and the completion of those events. This forecast provides the opportunity at any time during the clinical trial to generate a likelihood of meeting statistical endpoints 620. Such a forecast is critical for the study coordinator to monitor during the clinical trial and, as such, the coordinator is notified about progress 622. All of these actual and estimated T&E tables and changes are captured in a central database, the importance of which is further explained below.

Figure 7:
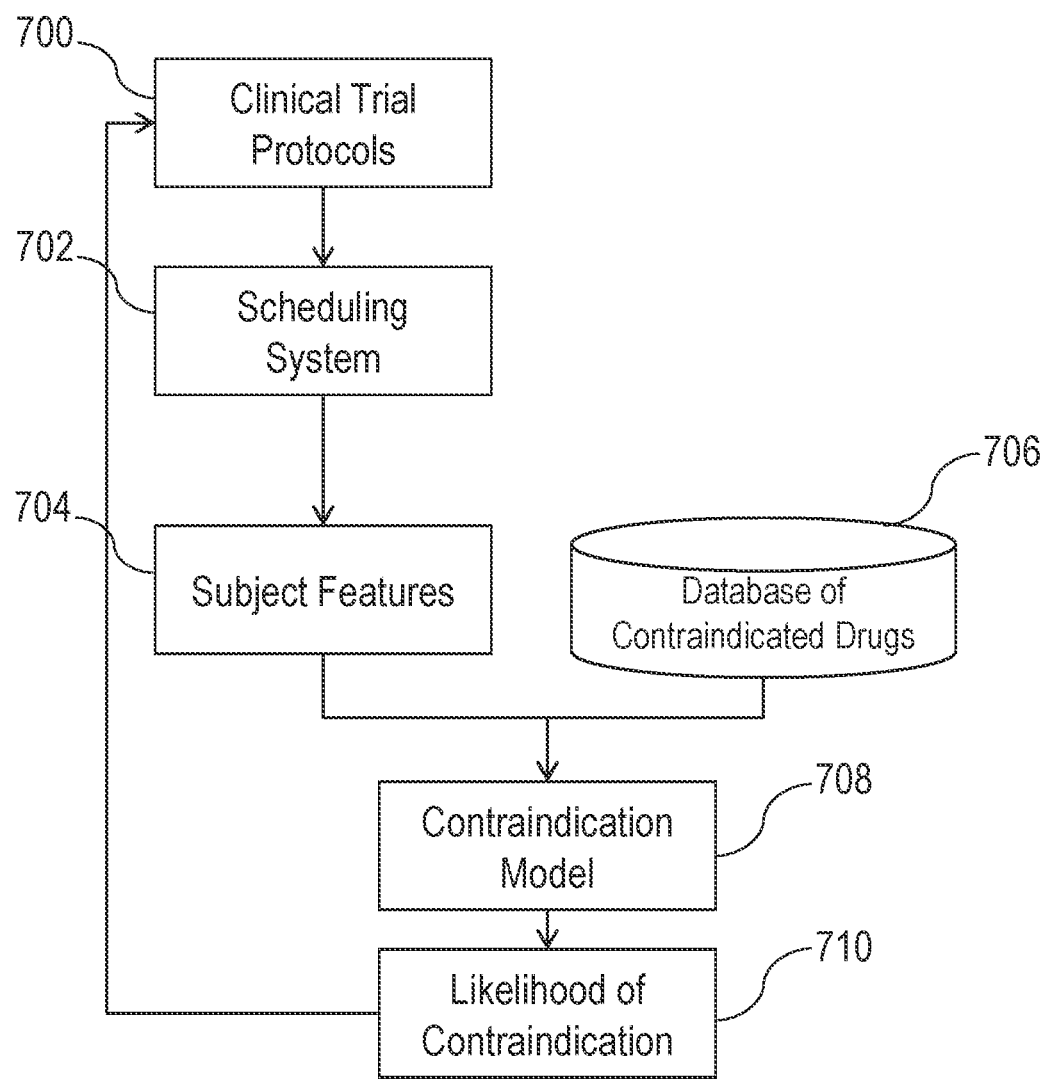
FIG. 7 illustrates an example of a contraindication model.

FIG. 7 illustrates an example of a contraindication model. When the clinical trial protocols 700 are provided to the scheduling system 702, features about the subjects 704 involved with each study site are collected. These features may include demographics, genomics, history of surgery, other medications, injuries, and any other relevant medical history. When combined with a database of contraindicated drugs 706, the system generates a contraindication model 708 that estimates the likelihood or determines the existence of a contraindication 710 for each subject based on his or her features and the previous knowledge of contraindicated drugs and subjects. A sufficiently high likelihood or known issue causes an update to the clinical trial to specifically reduce the likelihood of contraindication in the current subject and potentially future subjects enrolled in the trial. The process of mapping of subject features to contraindication likelihoods is itself maintained over time in a central database which can be used to further improve the contraindication models with time. Any contraindications based on medical, genetic, or surgical history may also be indicated.

Figure 8:
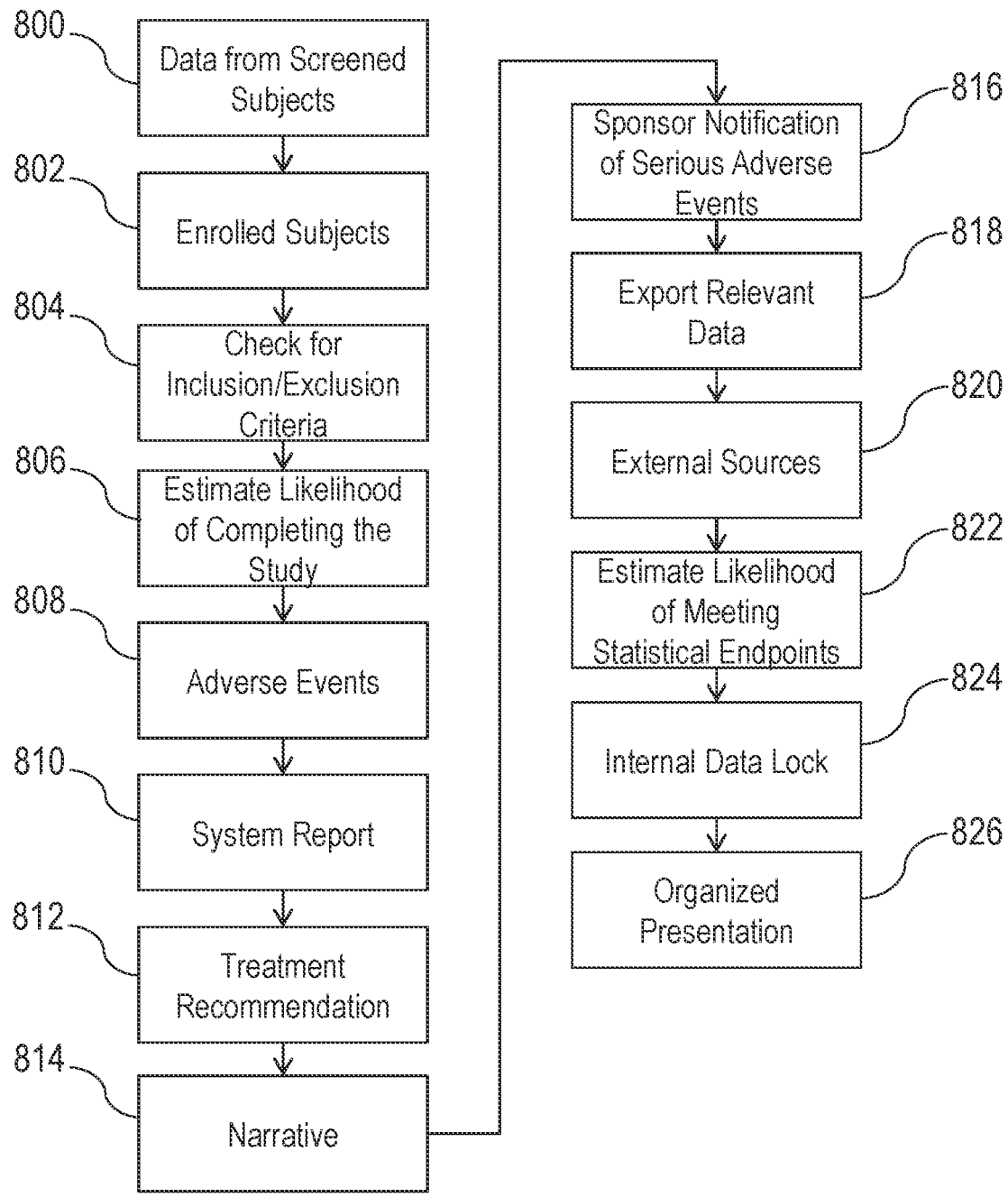
FIG. 8 is a flowchart for clinical trial information.

FIG. 8 is a flowchart for clinical trial information. When a clinical trial has started, the system works with the available data obtained from screened subjects 800. Subjects who are to be enrolled 802 are checked for inclusion/exclusion criteria 804. Based on the available information, the system may offer an estimated likelihood of completing the study 806. This estimate may be the result of a mathematical function derived using domain expertise, that is, human opinion, and machine learning, such as that accompanying a patient burden index as described earlier. The mathematical function may be a neural network or a rule-base of crisp or fuzzy rules, with various machine learning methods, including for example evolutionary algorithms, swarm optimization, and/or stochastic gradient descent. In the case of using evolutionary algorithms, potential combinations of rules can be scored based on how well the rules estimate the likelihood of study completion. Better-scoring rule sets can be retained as parents for new rule sets, created by varying those existing parent rule sets and/or recombining rule sets.

As a clinical trial proceeds, adverse events 808 such as primary endpoints, secondary endpoints, other endpoints, adverse events are stored in the system database, which checks for plausibility of being related to the study drug/device based on the information in the Investigator's Brochure and potentially other information that may be available, including the subject's personal history. The system offers a report 810 on the possibility of the adverse event being related to the study drug/device. This possibility may be based on machine learning algorithms, including neural networks, evolutionary algorithms, as well as fuzzy logic algorithms. Using data associated with known adverse events, logic can provide guidance on the probable relatedness of a drug to an existing adverse event. Fuzzy logic may be used to provide linguistic modifiers of subject history, such as "long-time user" of a particular drug or device, as well as a linguistic description of the possibility of relatedness beyond the typical not related, possibly related, probably related, or related, although this standard set may be what is needed to be reported officially. Where possible the system may offer a recommendation on treatment for an adverse event 812 based on standard of care, taking into account contra-indications, prospective outcomes, and the protocol of the clinical trial. Serious adverse events require a narrative 814, which is prompted by the system and stored in the system database. The sponsor is notified of all serious adverse events 816. All adverse event data are analyzed and combined with other available knowledge to provide possible insight to the principal investigator and sponsor.

If suitable permissions exist, the system may export relevant data 818 to identified external sources 820. The system may support interim analyses, including different analyses on adverse events, serious adverse events, adverse events of special interest, and fatalities. Based on interim analysis, the system may offer a likelihood of successfully meeting statistical endpoints 822. This may be accomplished using mathematical functions that assess the current rate of progress, the likelihood for continuing subjects to complete the trial or drop out, and remaining budget and time. As appropriate, the system may facilitate communication between subjects, as well as focus group support.

Internal data lock occurs 824 automatically once the last subject's data are recorded, or when the investigator so indicates. The system then processes the available data to provide an organized presentation 826 of the data to the principal investigator and sponsor. The data may be organized so as to facilitate transmission to the Food and Drug Administration, or other governing body. The data may also be organized so as to facilitate inclusion in a clinical study report.

Figure 9:
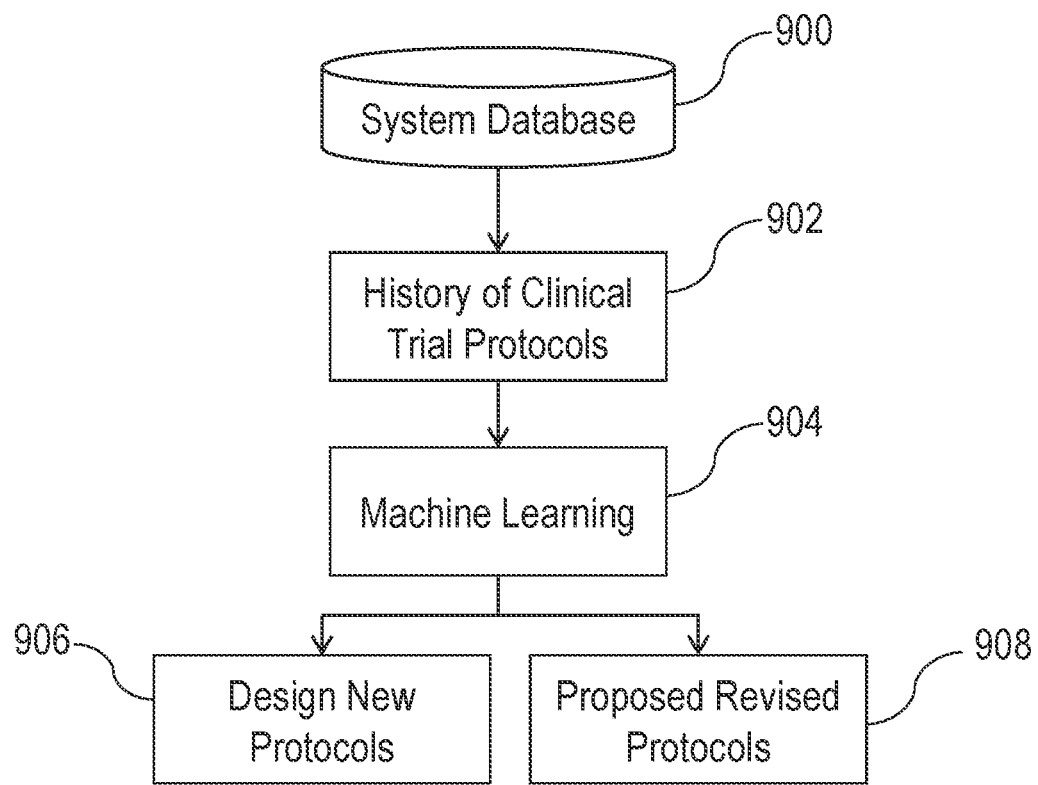
FIG. 9 is a flowchart for protocol design and optimization.

FIG. 9 is a flowchart for protocol design and optimization. As explained above, the central system database 900 contains a wide variety of data captured during each clinical trial setting. It is this database that also contains a history of clinical trial protocols 902 and their modification over time. In light of these data, machine learning 904 can be used to design new protocols 906 for future trials in order to improve success, and/or propose revised protocols 908 in an intelligent manner concurrent to each trial. For example, clustering algorithms can, in part, associate similarities between successful trials and between unsuccessful trials, extracting the similarities that can then be identified as being suitable or unsuitable for future trials. Neural networks may be used to assess the appropriateness of alternative study sites and principal investigators based on historical data regarding how many trials they have conducted or led, the types of trials, the propensity to meet desired enrollment numbers, the percentage of subjects who withdraw, costs, locations, and other factors.

Such an adaptive system is capable of autonomous learning about what time and events will lead to improvements in clinical trial design and management at reduced risk and cost. For example, if it is the case that a post-surgical patient is going to have a blood draw and will also be asked to report on perceived pain levels following surgery. It is standard practice to assess pain levels before doing the blood draw, so as not to confound the patient's pain assessment. It may be surmised that if this were not a standard protocol, that an adaptive autonomous learning system would be able to discern that patient-reported pain levels are generally higher when reported after a blood draw, rather than before.

Figure 10:
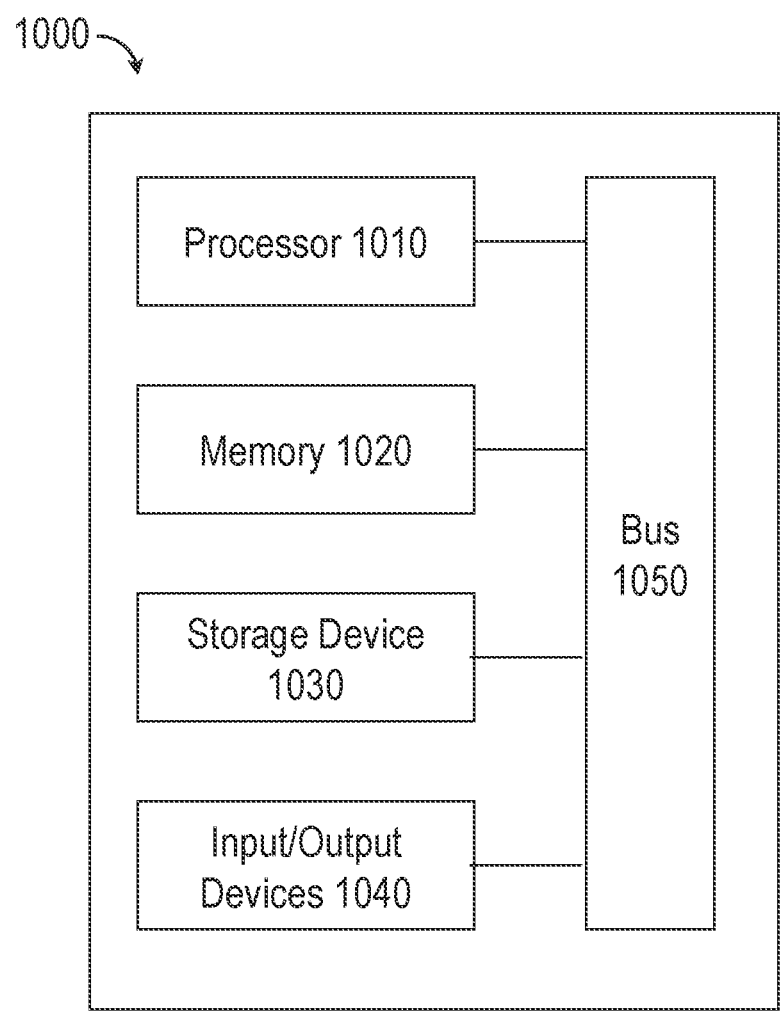
FIG. 10 is a block diagram illustrating a computing system consistent with implementations of the current subject matter.

FIG. 10 depicts a block diagram illustrating a computing system 1000 consistent with implementations of the current subject matter. Referring to FIGS. 2 and 10, the computing system 1000 can be used to implement the coordinator system depicted in FIG. 2, or any component therein, to, for example, calculate a patient burden index 216, a compliance score 218, or a reward to a user 220. Similarly, the computing system 1000 can be used to implement each of the systems and components in FIGS. 1-9.

As shown in FIG. 10, the computing system 1000 can include a processor 1010, a memory 1020, a storage device 1030, and input/output devices 1040. The processor 1010, the memory 1020, the storage device 1030, and the input/output devices 1040 can be interconnected via a system bus 1050. The processor 1010 is capable of processing instructions for execution within the computing system 1000. Such executed instructions can implement one or more components of, for example, the coordinator system depicted in FIG. 2, to, for example, calculate a patient burden index 216, a compliance score 218, or a reward to a user 220. In some implementations of the current subject matter, the processor 1010 can be a single-threaded processor. Alternately, the processor 1010 can be a multi-threaded processor. The processor 1010 is capable of processing instructions stored in the memory 1020 and/or on the storage device 1030 to display graphical information for a user interface provided via the input/output device 1040.

The memory 1020 is a computer readable medium such as volatile or non-volatile memory that stores information within the computing system 1000. The memory 1020 can store data structures representing configuration object databases, for example. The storage device 1030 is capable of providing persistent storage for the computing system 1000. The storage device 1030 can be a floppy disk device, a hard disk device, an optical disk device, or a tape device, or other suitable persistent storage means. The input/output device 1040 provides input/output operations for the computing system 1000. In some implementations of the current subject matter, the input/output device 1040 includes a keyboard and/or pointing device. In various implementations, the input/output device 1040 includes a display unit for displaying graphical user interfaces.

According to some implementations of the current subject matter, the input/output device 1040 can provide input/output operations for a network device. For example, the input/output device 1040 can include Ethernet ports or other networking ports to communicate with one or more wired and/or wireless networks (e.g., a local area network (LAN), a wide area network (WAN), the Internet).

In some implementations of the current subject matter, the computing system 1000 can be used to execute various interactive computer software applications that can be used for organization, analysis and/or storage of data in various (e.g., tabular) format (e.g., Microsoft Excel®, and/or any other type of software). Alternatively, the computing system 1000 can be used to execute any type of software applications. These applications can be used to perform various functionalities, e.g., machine learning, artificial intelligence, analytics, planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1040. The user interface can be generated and presented to a user by the computing system 1000 (e.g., on a computer screen monitor, etc.).

Figure 11:
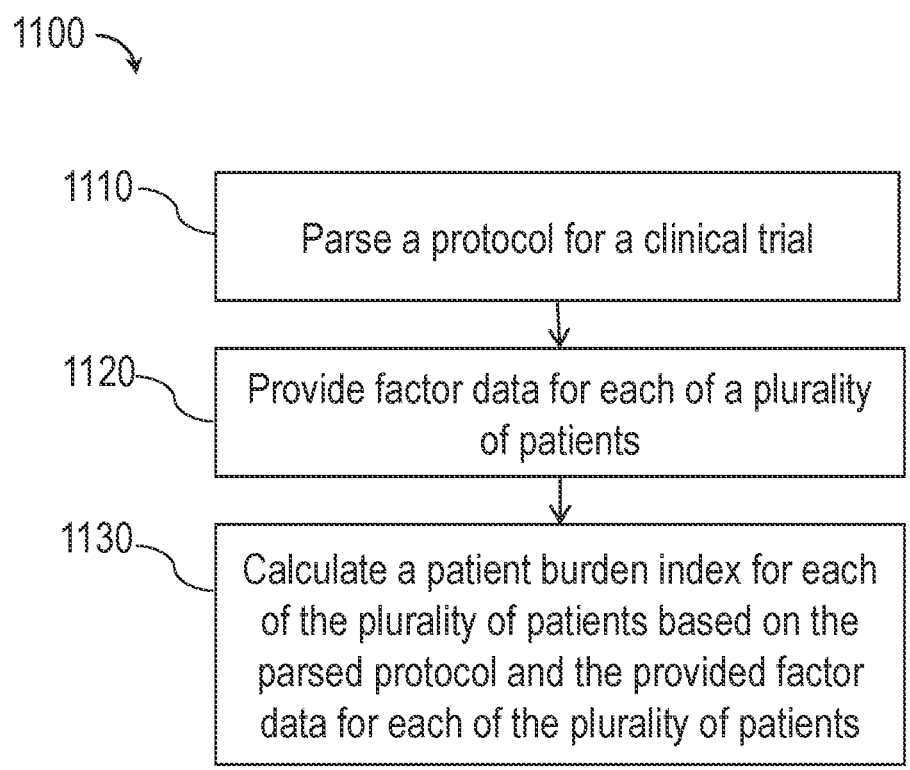
FIG. 11 is a flowchart of a process to calculate a patient burden.

FIG. 11 is a flowchart of a process 1100 for calculating a patient burden 216, in accordance with some example embodiments. Referring to FIG. 2, the process 1100 may be performed by the computing system 1000.

At 1110, the computing system 1000 parses a protocol for a clinical trial. In various embodiments, parsing the protocol for the clinical trial may include analyzing a protocol document using keyword analysis and pattern matching. In various embodiments, parsing the protocol for the clinical trial may include generating a schedule of actions to be taken in the clinical trial.

At 1120, the computing system 1000 provides factor data for each of a plurality of patients. The factor data may include patient data, trial cost data, trial time data, trial content data, trial schedule data, and/or trial conduct data. The patient data may include age, gender, insurance status, marital status, number of children, and/or insurance coverage. The trial cost data may include transportation cost, lost work cost, and/or unreimbursed medical costs. The trial time data may include travel time, waiting time, and/or direct trial participation time. The trial content data may include observation by trial clinician, monitoring of vital signs, and/or blood draws. The trial schedule data may include trial events at scheduled dates and times. The trial conduct data may include empathy of trial personnel, understandability of trial materials, rigidity of scheduling, physical discomfort associated with trial events, and/or fatigue associated with trial events.

At 1130, the computing system 1000 calculates a patient burden index for each of the plurality of patients based on the parsed protocol and the provided factor data for each of the plurality of patients. The patient burden index may correspond to an absolute level of burden on the patient participating in the trial, a probability of retention of the patient in the trial to completion, a probability that the patient will offer positive comments about the trial, and/or a probability that the patient will offer positive comments about a principal investigator or a staff member of the trial.

The method may further include training a machine learning system with a training observations of historic patient factor data and historic patient burden data. The machine learning system may include a neural network, a rule based system, a linear regression system, a non-linear regression system, a fuzzy logic system, a decision tree, a nearest neighbor classifier, and/or a statistical pattern recognition classifier. The neural network may further include input nodes, hidden nodes, and at least one output node, such as the neural network depicted in FIG. 3. Input nodes may be connected to hidden nodes. Hidden nodes may be connected to the at least one output node.

The method 1100 may include inputting the factor data for the plurality of patients into the trained neural network and outputting, from the at least one output node, the patient burden index for each of the plurality of patients. The method 1100 may further include generating a rule base that associates the patient factors with the patient burden index. The rule base may include fuzzy rules.

The method 1100 may further include modifying the protocol to reduce the patient burden index.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD), a light emitting diode (LED), or an organic light emitting diode (OLED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
   establishing, by one or more processors, a model trained using historical data of patients of one or more clinical trials, wherein the historical data comprises historic patient factor data of a first set of patients and historic patient burdens of the first set of patients, the model configured to receive as input factor data for one or more patients and provide as output a patient burden index for each of the one or more patients, wherein the model is trained by:
   inputting the historic patient factor data into the model and executing the model to output predicted patient burdens for the first set of patients; and
   adjusting one or more weights or parameters of the model based on a difference between the predicted patient burdens and the historic patient burdens;
   analyzing, by one or more processors, a document of a protocol for a clinical trial to identify a schedule of actions to be taken in the clinical trial for a second set of patients;
   identifying, by one or more processors, a set of factor data for each patient of the second set of patients to participate in the schedule of actions of the clinical trial;
   inputting, by the one or more processors, the set of factor data for each patient of the second set of patients into the model;
   receiving, by the one or more processors, output from the model identifying the patient burden index for each of the second set of patients, the patient burden index providing a quantitative measure of impact of the protocol on each of the second set of patients; and
   identifying, by the one or more processors, a modification to the protocol to adjust the patient burden index for one or more patients of the second set of patients.

2. The method of claim 1, wherein the factor data comprises one or more of the following: patient data, trial cost data, trial time data, trial schedule data, and trial conduct data.

3. The method of claim 1, further comprising: generating, by the one or more processors, a rule that associates the factor data with the patient burden index.

4. The method of claim 1, further comprising: sending, by the one or more processors to a user, a notification based on the schedule of actions.

5. The method of claim 4, wherein sending the notification is responsive to determining that an action of the schedule of actions is not completed at a time according to the schedule of actions.

6. The method of claim 4, wherein the notification comprises:
   a notification to send, to one or more patients of the second set of patients, materials for the clinical trial;
   a notification to adjust the schedule of actions based on an event;
   a notification of an event; or
   a notification to remind one or more patients of the second set of patients to complete an action of the schedule of actions.

7. The method of claim 1, further comprising:
   storing, by the one or more processors in a database, an indication of an event responsive to determining that an action of the schedule of actions is not completed at a time according to the schedule of actions; and
   determining, by the one or more processors, a recommendation for the event.

8. The method of claim 7, wherein the event comprises:
   an adverse event;
   a treatment-emergent event; or
   a protocol deviation.

9. The method of claim 1, further comprising:
   updating, by the one or more processors, sets of factor data for second one or more patients of the second set of patients based on one or more events; and
   executing, by the one or more processors using the updated sets of factor data as input, the model to calculate a second patient burden index for each patient of the second one or more patients of the second set of patients.

10. The method of claim 9, wherein the one or more events comprises at least one of a reminder, an action of the schedule of actions, or failure to perform an action of the schedule of actions.

11. The method of claim 1, wherein identifying the schedule of actions further comprises: calculating the schedule of actions based on an algorithm, the algorithm comprising either a greedy algorithm or an evolutionary algorithm.

12. The method of claim 1, further comprising:
analyzing, by the one or more processors during the clinical trial, one or more events; and
determining a likelihood of meeting one or more endpoints of the clinical trial by the end of the clinical trial.

13. A system, comprising:
one or more processors, coupled to memory, to:
establish a model trained using historical data of patients of one or more clinical trials, wherein the historical data comprises historic patient factor data of a first set of patients and historic patient burdens of the first set of patients, the model configured to receive as input factor data for one or more patients and provide as output a patient burden index for each of the one or more patients, wherein the model is trained by:
inputting the historic patient factor data into the model and executing the model to output predicted patient burdens for the first set of patients; and
adjusting one or more weights or parameters of the model based on a difference between the predicted patient burdens and the historic patient burdens;
analyze a document of a protocol for a clinical trial to identify a schedule of actions to be taken in a clinical trial for a second set of patients;
identify a set of factor data for each patient of the second set of patients to participate in the schedule of actions of the clinical trial;
input the set of factor data for each patient of the second set of patients into the model;
receive output from the model identifying the patient burden index for each of the second set of patients, the patient burden index providing a quantitative measure of impact of the protocol on each of the second set of patients; and
identify a modification to the protocol to adjust the patient burden index for one or more patients of the second set of patients.

14. The system of claim 13, the one or more processors further to: generate a rule that associates the factor data with the patient burden index.

15. The system of claim 13, the one or more processors further to: send a notification based on the schedule of actions and responsive to determining that an action of the schedule of actions is not completed at a time according to the schedule of actions.

16. The system of claim 13, further comprising:
storing, by the one or more processors in a database, an indication of an event responsive to determining that an action of the schedule of actions is not completed at a time according to the schedule of actions; and
determining, by the one or more processors, a recommendation for the event.

17. The system of claim 13, further comprising:
updating, by the one or more processors, sets of factor data for second one or more patients of the second set of patients based on one or more events; and
executing, by the one or more processors using the updated sets of factor data for the second one or more patients of the second set of patients as input, the model to calculate a second patient burden index for each patient of the second one or more patients of the second set of patients.

18. The system of claim 13, further comprising:
analyzing, by the one or more processors during the clinical trial, one or more events; and
determining a likelihood of meeting one or more endpoints of the clinical trial by the end of the clinical trial.

19. A non-transitory computer readable storage medium comprising instructions stored thereon that, when executed by a processor, cause the processor to:
establish a model trained using historical data of patients of one or more clinical trials, wherein the historical data comprises historic patient factor data of a first set of patients and historic patient burdens of the first set of patients, the model configured to receive as input factor data for one or more patients and provide as output a patient burden index for each of the one or more patients, wherein the model is trained by:
inputting the historic patient factor data into the model and executing the model to output predicted patient burdens for the first set of patients; and
adjusting one or more weights or parameters of the model based on a difference between the predicted patient burdens and the historic patient burdens;
analyze a document of a protocol for a clinical trial to identify a schedule of actions to be taken in a clinical trial for a second set of patients;
identify a set of factor data for each of the second set of patients to participate in the schedule of actions of the clinical trial;
input the set of factor data into the model;
receive output from the model identifying the patient burden index for each of the second set of patients, the patient burden index providing a quantitative measure of impact of the protocol on each of the second set of patients; and
identify a modification to the protocol to adjust the patient burden index for one or more patients of the second set of patients.

20. The medium of claim 19, wherein the instructions stored thereon further cause the processor to: generate a rule that associates the factor data with the patient burden index.

* * * * *